United States Patent
Kashihara et al.

(10) Patent No.: US 10,371,612 B2
(45) Date of Patent: Aug. 6, 2019

(54) PREPREG, METAL-CLAD LAMINATED PLATE, WIRING BOARD, AND METHOD FOR MEASURING THERMAL STRESS OF WIRING BOARD MATERIAL

(71) Applicant: Panasonic Intellectual Property Management Co., Ltd., Osaka (JP)

(72) Inventors: Keiko Kashihara, Osaka (JP); Hiroharu Inoue, Osaka (JP); Shingo Yoshioka, Osaka (JP); Takashi Hoshi, Fukushima (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 15/757,002

(22) PCT Filed: Sep. 9, 2016

(86) PCT No.: PCT/JP2016/004107
§ 371 (c)(1),
(2) Date: Mar. 2, 2018

(87) PCT Pub. No.: WO2017/051510
PCT Pub. Date: Mar. 30, 2017

(65) Prior Publication Data
US 2018/0275031 A1 Sep. 27, 2018

(30) Foreign Application Priority Data

Sep. 25, 2015 (JP) .................................. 2015-187575

(51) Int. Cl.
*B32B 5/28* (2006.01)
*C08J 5/24* (2006.01)
(Continued)

(52) U.S. Cl.
CPC ................. *G01N 3/18* (2013.01); *B32B 5/28* (2013.01); *B32B 15/08* (2013.01);
(Continued)

(58) Field of Classification Search
CPC .... G01N 3/08; G01N 3/18; G01N 2203/0017; G01N 2203/0057; H05K 1/0271; H05K 2201/068; B32B 2457/08
See application file for complete search history.

(56) References Cited

U.S. PATENT DOCUMENTS 6,569,371 B1 * 5/2003 Asari ...................... B29C 70/52
156/229
6,811,638 B2 * 11/2004 Close ........................ B32B 5/04
156/164

(Continued)

FOREIGN PATENT DOCUMENTS

JP 2011-155085 8/2011
JP 2014-111719 6/2014
(Continued)

OTHER PUBLICATIONS

International Search Report of PCT application No. PCT/JP2016/004107 dated Dec. 6, 2016.

*Primary Examiner* — William H. Mayo, III
*Assistant Examiner* — Rhadames Alonzo Miller
(74) *Attorney, Agent, or Firm* — Greenblum & Bernstein, P.L.C.

(57) ABSTRACT

A prepreg includes a resin layer constituted by a half-cured product of a thermosetting resin composition, and a fibrous substrate provided in the resin layer. A prepreg test piece that is a cured product obtained by heat curing the thermosetting resin composition has a maximum value of 400 kPa or less for thermal shrinkage stress measured by a predetermined thermal stress test.

11 Claims, 2 Drawing Sheets

(51) Int. Cl.
    *G01N 3/18*    (2006.01)
    *H05K 1/02*    (2006.01)
    *H05K 1/03*    (2006.01)
    *H05K 3/06*    (2006.01)
    *B32B 15/08*    (2006.01)
    *B32B 37/10*    (2006.01)
    *B32B 38/00*    (2006.01)

(52) U.S. Cl.
    CPC ............ *B32B 37/1018* (2013.01); *C08J 5/24* (2013.01); *H05K 1/0271* (2013.01); *H05K 1/0373* (2013.01); *H05K 3/06* (2013.01); *B32B 37/10* (2013.01); *B32B 2038/0076* (2013.01); *B32B 2309/02* (2013.01); *B32B 2309/105* (2013.01); *B32B 2457/08* (2013.01); *C08J 2363/00* (2013.01); *G01N 2203/0017* (2013.01); *G01N 2203/0057* (2013.01); *H05K 1/038* (2013.01); *H05K 2201/0209* (2013.01); *H05K 2201/068* (2013.01)

(56) References Cited

U.S. PATENT DOCUMENTS

| | | | |
|---|---|---|---|
| 2004/0185733 A1* | 9/2004 | Murai | B29C 70/22 442/265 |
| 2005/0160829 A1* | 7/2005 | Renieri | G01N 3/08 73/729.1 |
| 2008/0036097 A1* | 2/2008 | Ito | C08L 63/00 257/778 |
| 2009/0312960 A1* | 12/2009 | Dang | G06F 17/5018 702/42 |
| 2011/0319564 A1* | 12/2011 | Corley | C08G 59/5006 525/132 |
| 2013/0063570 A1* | 3/2013 | Michopoulos | G01B 11/165 348/47 |
| 2013/0220024 A1* | 8/2013 | Osborne | G01M 5/005 73/849 |
| 2014/0000948 A1 | 1/2014 | Nagai et al. | |
| 2014/0303306 A1* | 10/2014 | Kajiwara | C08J 5/042 524/496 |
| 2015/0037589 A1* | 2/2015 | Inoue | C08G 59/245 428/418 |
| 2015/0075852 A1* | 3/2015 | Inoue | C09D 163/00 174/258 |
| 2016/0047723 A1* | 2/2016 | Esposito | G01N 3/08 73/818 |
| 2016/0258862 A1* | 9/2016 | Shin | G01N 19/04 |

FOREIGN PATENT DOCUMENTS

| | | | | |
|---|---|---|---|---|
| JP | WO 2014141689 A1 * | 9/2014 | ......... | C09D 163/00 |
| JP | 2015-044969 | 3/2015 | | |
| JP | 2015-086293 | 5/2015 | | |
| WO | 2012/099134 | 7/2012 | | |
| WO | 2014/141689 | 9/2014 | | |

* cited by examiner

PREPREG, METAL-CLAD LAMINATED PLATE, WIRING BOARD, AND METHOD FOR MEASURING THERMAL STRESS OF WIRING BOARD MATERIAL

This application is a U.S. national stage application of the PCT International Application No. PCT/JP2016/004107 filed on Sep. 9, 2016, which claims the benefit of foreign priority of Japanese patent application 2015-187575 filed on Sep. 25, 2015, the contents all of which are incorporated herein by reference.

TECHNICAL FIELD

The present disclosure relates to a prepreg, a metal-clad laminate, a wiring board, and a method for measuring thermal stress of a wiring board material.

BACKGROUND

Accompanying reduction in size and thickness of electronic devices, electronic components each having a surface mount package are being increasingly used in these electronic devices. Specific examples of such a package include a package in which a semiconductor chip is mounted on a board, such as a Chip On Board (COB) package. Such a package has a structure in which a semiconductor chip is bonded to a board. Therefore, due to a difference in coefficient of thermal expansion (CTE) between the semiconductor chip and the board, deformation such as warpage of a package sometimes occurs by a change in temperature. Further, in such a package, an increase in warpage increases power for peeling the semiconductor chip from the board so that bonding reliability between the semiconductor chip and the board is decreased.

Furthermore, electronic devices are further required of reduction in size and thickness. In order to satisfy such a requirement, reduction in size and thickness of electronic components have been attempted, and along with this attempt, reduction in thickness of a board constituting a package of an electronic component has been studied. Such a board having a reduced thickness is likely to generate the warpage, and thus suppressing the generation of the warpage has been further required.

Additionally, in order to make electronic devices multi-functional, it is necessary to increase a number of electronic components to be incorporated. For satisfying this requirement, a form of package known as a Package on Package (PoP) is employed in which a plurality of sub-packages are laminated and mounted on a board, followed by further integrating the sub-packages and the board into a single package. For example, this PoP is frequently employed in portable terminal devices such as a smartphone and a tablet computer. Since this PoP is a form in which a plurality of sub-packages are laminated, the bonding reliability between sub-packages, for example, has been important. In order to increase the bonding reliability, reduction of the warpage in each package used as a sub-package is required.

For the reasons described above, even when the board is used as a thin board in a package, a board material for producing a board whose warpage, for example, can be sufficiently suppressed has been developed. Examples of such a board material include a resin composition described in International Publication No. WO 2012/099134.

International Publication No. WO 2012/099134 discloses a resin composition containing a maleimide compound having at least two N-substituted maleimide groups per one molecular structure, and a silicone compound having at least one amino group per one molecular structure.

SUMMARY

A prepreg according to one aspect of the present disclosure includes a resin layer constituted by a half-cured product of a thermosetting resin composition, and a fibrous substrate provided in the resin layer. A prepreg test piece that is a cured product obtained by heat curing the thermosetting resin composition has a maximum value of 400 kPa or less for thermal shrinkage stress measured by a following thermal stress test.

[Thermal Stress Test]

A prepreg test piece having a thickness of 0.1 mm is held at both ends by jigs and measured for tensile stress between the jigs that is defined as thermal shrinkage stress. The tensile stress is measured during a period which a temperature of the prepreg test piece is lowered from 260° C. to normal temperature after the prepreg test piece is heated to a temperature of 260° C. while a distance between the jigs is changed in a range from 0.01 ppm/° C. to 5 ppm/° C., inclusive, by allowing the jigs to come closer to each other.

Further, with regard to the prepreg, the prepreg test piece that is the cured product obtained by heat curing the thermosetting resin composition preferably has a maximum value of 100 kPa or less for thermal expansion stress measured by a following thermal stress test.

[Thermal Stress Test]

A prepreg test piece having a thickness of 0.1 mm is held at both ends by jigs and measured for tensile stress between the jigs that is defined as thermal expansion stress. The tensile stress is measured during a period which a temperature of the prepreg test piece is raised from normal temperature to 260° C. while a distance between the jigs is changed in a range from 0.01 ppm/° C. to 5 ppm/° C., inclusive, by allowing the jigs to separate from each other.

A prepreg according to another aspect of the present disclosure includes a resin layer constituted by a half-cured product of a thermosetting resin composition, and a fibrous substrate provided in the resin layer. A prepreg test piece that is a cured product obtained by heat curing the thermosetting resin composition has a maximum value of 100 kPa or less for thermal expansion stress measured by a following thermal stress test.

[Thermal Stress Test]

A prepreg test piece having a thickness of 0.1 mm is held at both ends by jigs and measured for tensile stress between the jigs that is defined as thermal expansion stress. The tensile stress is measured during a period which a temperature of the prepreg test piece is raised from normal temperature to 260° C. while a distance between the jigs is changed in a range from 0.01 ppm/° C. to 5 ppm/° C., inclusive, by allowing the jigs to separate from each other.

In any one of the prepregs, the thermosetting resin composition preferably contains at least one resin selected from the group consisting of an epoxy resin, a polyimide resin, polyphenylene oxide (PPO), a radically polymerizable resin, and modified resins thereof. Further, the thermosetting resin composition preferably contains two or more resins selected from the group.

In any of the prepregs, the fibrous substrate is preferably woven fabric or nonwoven fabric.

In any one of the prepregs, the thermosetting resin composition preferably further contains an inorganic filler.

A metal-clad laminate according to an aspect of the present disclosure includes a cured product of the prepreg described above and metal foil provided on at least one of upper surface of the cured product of the prepreg and lower surface of the cured product of the prepreg. Further, the metal foil is preferably provided on both upper surface of the cured product of the prepreg and lower surface of the cured product of the prepreg.

A wiring board according to an aspect of the present disclosure includes a cured product of the prepreg described above and a conductor pattern provided as a circuit on a surface of the cured product of the prepreg.

A method for measuring thermal stress of a wiring board material according to an aspect of the present disclosure includes: holding both ends of a test piece constituted by a wiring board material by jigs, respectively; and measuring tensile stress between the jigs which is defined as thermal shrinkage stress, the tensile stress being measured during a period which a temperature of the test piece is lowered from 260° C. to normal temperature after the test piece is heated to a temperature of 260° C. while a distance between the jigs is changed in a range from 0.01 ppm/° C. to 5 ppm/° C., inclusive, by allowing the jigs to come closer to each other.

A method for measuring thermal stress of a wiring board material according to another aspect of the present disclosure includes: holding both ends of a test piece constituted by a wiring board material by jigs, respectively, and measuring tensile stress between the jigs which is defined as thermal expansion stress, the tensile stress being measured during a period which a temperature of the test piece is raised from normal temperature to 260° C. while a distance between the jigs is changed in a range from 0.01 ppm/° C. to 5 ppm/° C., inclusive, by allowing the jigs to separate from each other.

According to the present disclosure, it is possible to provide a prepreg capable of giving a molded body that sufficiently suppresses generation of warpage. In addition, according to the present disclosure, there are provided a metal-clad laminate and a wiring board that include this prepreg. Further, the present disclosure provides a new method for measuring thermal stress of a wiring board material.

DESCRIPTION OF EMBODIMENTS

Figure 1:
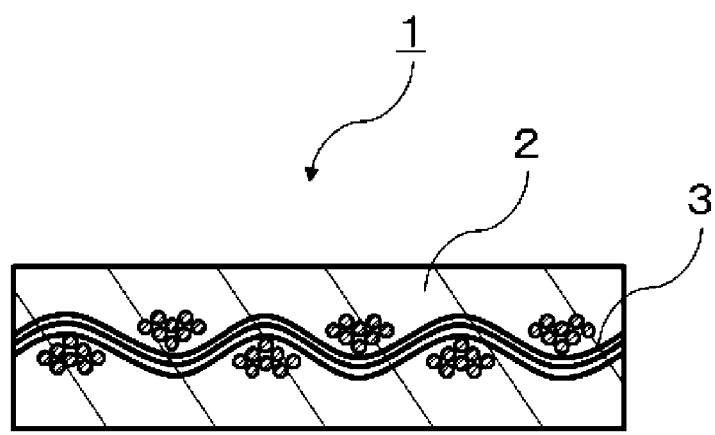
FIG. 1 is a schematic sectional view illustrating a prepreg according to an exemplary embodiment.

Before describing exemplary embodiments of the present disclosure, a problem in a conventional device will be briefly described. International Publication No. WO 2012/099134 describes that it is possible to produce a multilayer wiring board having excellent properties of glass-transition temperature, coefficient of thermal expansion, solder heat resistance, and warpage characteristics, and the multilayer wiring board is useful as a wiring board for electronic devices.

A board obtained by using a resin composition described in International Publication No. WO 2012/099134 cannot sometimes give a package that sufficiently suppresses deformation such as warpage generated due to a change in temperature.

As described above, a bonded body obtained by bonding two or more members made of different materials causes, due to a difference in coefficient of thermal expansion between the members, stress in a direction in which warpage is generated due to a change in temperature. Therefore, the bonded body obtained by bonding two or more members made of different materials sometimes generates, in the same manner as in a case of the package described above, a failure of generating warpage due to a change in temperature. Also, a failure of not maintaining a bonding state between the members sometimes occurs. Occurrence of such a failure is being required to be suppressed.

According to a study by the inventors of the present invention, board materials, such as the resin composition described in International Publication No. WO 2012/099134, that have been proposed so far as board materials for reducing the warpage of a package have been developed for purpose of increasing an elastic modulus and decreasing the coefficient of thermal expansion of a board. An increase in elastic modulus is considered to increase rigidity of the board itself to make the board less likely to be bent, so that generation of the warpage can be suppressed. A decrease in the coefficient of thermal expansion is considered to reduce a difference in the coefficient of thermal expansion between the board and a semiconductor chip to reduce power for bending the board.

However, a relationship between suppression of the warpage and the thermal stress of a semiconductor package has not been reported.

The present disclosure has been made in view of such circumstances and provides, by controlling the thermal stress of a material, a prepreg capable of giving a molded body that sufficiently suppresses generation of the warpage. The present disclosure also provides a metal-clad laminate and a wiring board that include this prepreg. Further, the present disclosure provides a new method for measuring thermal stress of a wiring board material.

The inventors of the present invention have focused on the relationship between suppression of the warpage and the thermal stress of a semiconductor package, and, by conducting various studies, have found that controlling the thermal stress of a board material can provide a prepreg capable of giving a molded body that sufficiently suppresses generation of the warpage. On the basis of this finding, further studies have been conducted to attain the present disclosure.

Hereinafter, the exemplary embodiments according to the present disclosure will be described. The present disclosure, however, is not limited to these exemplary embodiments.

FIG. 1 is a schematic sectional view illustrating a prepreg according to an exemplary embodiment. Prepreg 1 includes resin layer 2 formed of a half-cured product of a thermosetting resin composition, and fibrous substrate 3 provided in resin layer 2, and thermal stress (thermal shrinkage stress and/or thermal expansion stress) is controlled that is measured by a predetermined thermal stress test. In the present specification, prepreg 1 that includes resin layer 2 formed of a half-cured product of a thermosetting resin composition, and fibrous substrate 3 provided in resin layer 2 refers to prepreg 1 formed by impregnating fibrous substrate 3 with the thermosetting resin composition and heating and drying the thermosetting resin composition to a half-cured state (so-called a stage B state).

It should be noted that the half-cured product of a thermosetting resin composition in the present exemplary embodiment refers to the thermosetting resin composition in a middle stage of a curing reaction, which once melts and proceeds with a curing reaction when subjected to a rise in temperature. In addition, the cured product of a thermosetting resin composition refers to the thermosetting resin composition which does not melt even when heated due to cross-linking of a resin by proceeding with a curing reaction.

Prepreg 1 has a property so that prepreg test piece 4, which is a cured product obtained by further heating to cure the thermosetting resin composition contained in prepreg 1, has a maximum value of 400 kPa or less for thermal shrinkage stress measured when lowered in temperature from 260° C. to normal temperature. Or prepreg 1 has a property so that prepreg test piece 4 has a maximum value of 100 kPa or less for thermal expansion stress measured when raised in temperature from normal temperature to 260° C. In a more preferable exemplary embodiment, prepreg 1 preferably has a property so that prepreg test piece 4 has a maximum value of 400 kPa or less for thermal shrinkage stress in the temperature lowering time and a maximum value of 100 kPa or less for thermal expansion stress in the temperature rising time.

Hereinafter, first, measurement of the thermal stress in the present exemplary embodiment is described.

<Thermal Shrinkage Stress>

In one exemplary embodiment of the present disclosure, prepreg test piece 4 that is a cured product obtained by heat curing the thermosetting resin composition has a maximum value of 400 kPa or less for thermal shrinkage stress measured by a following thermal stress test.

[Thermal Stress Test]

Prepreg test piece 4 having a thickness of 0.1 mm is held at both ends by jigs. And tensile stress between the jigs, which is defined as thermal shrinkage stress, is measured. The tensile stress is measured during a period which a temperature of prepreg test piece 4 is lowered from 260° C. to normal temperature after prepreg test piece 4 is heated to a temperature of 260° C. while a distance between the jigs is changed in a range from 0.01 ppm/° C. to 5 ppm/° C., inclusive, by allowing the jigs to come closer to each other.

Figure 2:
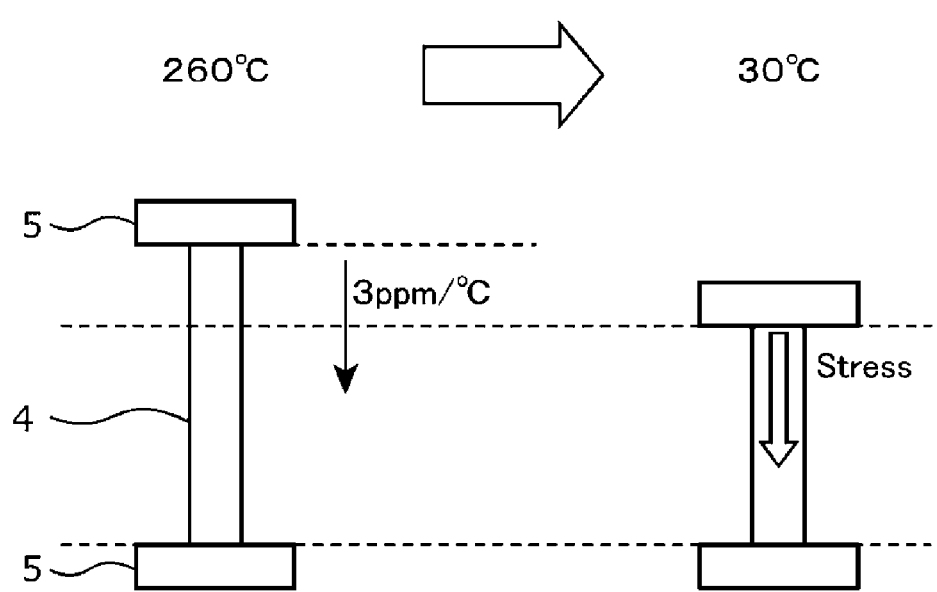
FIG. 2 is a schematic view for describing one example of a method for measuring thermal stress in the present disclosure.

Specifically, as shown in FIG. 2, for example, prepreg test piece 4 that has been obtained through heat curing is held at both ends by jigs 5, and an initial load of, for example, 20 mN is applied. Then, prepreg test piece 4 is heated to a temperature of 260° C., and then a temperature of prepreg test piece 4 is lowered from 260° C. to normal temperature (about 30° C.) at a temperature lowering rate ranging approximately from 10° C./min to 20° C./min, inclusive. And in the meantime tensile stress is measured while a distance between jigs 5 is changed in a range from 0.01 ppm/° C. to 5 ppm/° C., inclusive, (the drawing shows an example of 3 ppm/° C.) by allowing the jigs to come closer to each other.

The tensile stress can be derived by a following equation.

Stress (kPa)=((Load at 30° C. (mN))−(Load at 260° C. (mN)))/Sectional area of prepreg test piece (mm2)

Then, the maximum value of thermal shrinkage stress is obtained, defining the derived tensile stress as the thermal shrinkage stress.

Prepreg 1 according to the present exemplary embodiment has a property so that a maximum value of the above thermal shrinkage stress is 400 kPa or less. This makes it possible to provide a board material capable of sufficiently suppressing generation of the warpage of a board even when the board is subjected to a change in temperature. More preferably, prepreg 1 has a property so that a maximum value of the above thermal shrinkage stress is 200 kPa or less.

In the measurement method described above, the measurement is performed while the distance between jigs 5 is changed in a range from 0.01 ppm/° C. to 5 ppm/° C., inclusive, by allowing the jigs to come closer to each other. The change in the distance between jigs 5 simulates linear shrinkage of another member, such as a semiconductor, to be mounted on a board in temperature lowering time. By using prepreg 1 according to the present exemplary embodiment that has a property so that a maximum value of the thermal shrinkage stress measured under such conditions is 400 kPa or less, deformation, such as warpage, that is generated due to, for example, a change in temperature is considered to be sufficiently suppressed even when the board is bonded to another member such as a semiconductor chip.

For the measurement of the tensile stress, there can be used, for example, a thermomechanical analysis apparatus (TMA).

<Thermal Expansion Stress>

In one exemplary embodiment of the present disclosure, prepreg test piece 4 that is a cured product obtained by heat curing the thermosetting resin composition has a maximum value of 100 kPa or less for thermal expansion stress measured by a following thermal stress test.

[Thermal Stress Test]

Prepreg test piece 4 having a thickness of 0.1 mm is held at both ends by jigs 5. And tensile stress between the jigs, which is defined as thermal expansion stress, is measured. The tensile stress is measured during a period which a temperature of prepreg test piece 4 is raised from normal temperature to 260° C. while a distance between jigs 5 is changed in a range from 0.01 ppm/° C. to 5 ppm/° C., inclusive, by allowing the jigs to separate from each other.

Specifically, for example, prepreg test piece 4 that has been obtained through heat curing is held at both ends by jigs 5, and an initial load of, for example, 20 mN is applied. Then, prepreg test piece 4 is held at normal temperature (30° C.) for 1 to 5 minutes, and then a temperature of prepreg test piece 4 is raised in temperature from normal temperature to 260° C. at a temperature rising rate ranging approximately from 10° C./min to 20° C./min, inclusive. And in the meantime tensile stress is measured while a distance between jigs 5 is changed in a range from 0.01 ppm/° C. to 5 ppm/° C., inclusive, by allowing the jigs to separate from each other.

The tensile stress can be derived by a following equation.

Stress (kPa)=((Maximum load)−(Load at 30° C. (mN)))/Sectional area of prepreg test piece (mm2)

It should be noted that the maximum load in the equation means a local maximal value in a temperature-stress curve. Then, the maximum value of thermal expansion stress is obtained, defining the derived tensile stress as the thermal expansion stress.

Prepreg 1 according to the present exemplary embodiment has a property so that a maximum value of the above thermal expansion stress is 100 kPa or less. This makes it possible to provide a board material capable of sufficiently suppressing generation of the warpage of a board even when the board is subjected to a change in temperature. More preferably, prepreg 1 has a property so that a maximum value of the above thermal expansion stress is 50 kPa or less.

In the measurement method described above, the measurement is performed while the distance between jigs 5 is changed in a range from 0.01 ppm/° C. to 5 ppm/° C., inclusive, by allowing the jigs to separate from each other. The change in the distance between jigs 5 simulates linear expansion of another member, such as a semiconductor, to be mounted on a board in temperature rising time. By using prepreg 1 according to the present exemplary embodiment that has a property so that a maximum value of the thermal expansion stress measured under such conditions is 100 kPa or less, deformation, such as warpage, that is generated by, for example, a change in temperature is considered to be sufficiently suppressed even when the board is bonded to another member such as a semiconductor chip.

For the measurement of the tensile stress, there can be used, for example, a thermomechanical analysis apparatus (TMA).

<Prepreg>

The thermosetting resin composition used for prepreg 1 according to the present exemplary embodiment is not particularly limited in terms of composition as long as the thermosetting resin composition is a resin composition that satisfies the characteristics described above. Preferably, the resin composition of the present exemplary embodiment contains at least a thermosetting resin and a curing agent for the thermosetting resin. The thermosetting resin composition may further contain, for example, a resin other than the thermosetting resin, and an inorganic filler.

The thermosetting resin may be a low molecular weight component whose cured product by curing becomes a resin, or may be a resin capable of giving a cured product through, for example, an increase in molecular weight or formation of a network structure by curing. Specifically, the thermosetting resin is not particularly limited, but examples of the thermosetting resin include an epoxy resin, a polyimide resin, polyphenylene oxide (PPO), a radically polymerizable resin, a phenol resin, a cyanate ester resin, a vinyl ester resin, an urea resin, a diallyl phthalate resin, a melanin resin, a guanamine resin, an unsaturated polyester resin, a melamine-urea co-condensation resin, and modified resins of these resins. These thermosetting resins may be used alone or in combination of two or more thermosetting resins. Further, among the thermosetting resins described above, preferable examples are at least one or two or more resins selected from the group consisting of an epoxy resin, a polyimide resin, polyphenylene oxide (PPO), a radically polymerizable resin, and modified resins of these resins. These thermosetting resins are likely to give a molded body having the characteristics described above.

The epoxy resin is not particularly limited as long as the epoxy resin is an epoxy resin used as a material for various boards that can be used for production of laminates and circuit boards. Specific examples of the epoxy resin include a naphthalene-type epoxy resin, a cresol novolac-type epoxy resin, a bisphenol A type epoxy resin, a bisphenol F type epoxy resin, a bisphenol S type epoxy resin, a phenol novolac-type epoxy resin, an alkyl phenol novolac-type epoxy resin, an aralkyl-type epoxy resin, a biphenol-type epoxy resin, a dicyclopentadiene-type epoxy resin, an epoxidized product of a condensation product of a phenol with an aromatic aldehyde having a phenolic hydroxyl group, triglycidylisocyanurate, and an alicyclic epoxy resin. These epoxy resins may be used alone or in combination of two or more epoxy resins. Among these epoxy resins, a naphthalene-type epoxy resin and the like are preferable.

The polyimide resin is not particularly limited as long as the polyimide resin is a polyimide resin used as a material for various boards that can be used for production of laminates and circuit boards. Specific examples of the polyimide resin include a polyamide-imide resin and a polymaleimide resin. More specific examples of the polyimide resin include imide resins obtained with use of, for example, phenylmethane maleimide, bisallylnadiimide, N,N-ethylenebismaleimide, N,N-hexamethylenebismaleimide, N,N-metaphenylenebismaleimide, N,N-paraphenylenebismaleimide, N,N-4,4-diphenylmethanebismaleimide, N,N-4,4-diphenyletherbismaleimide, N,N-4,4-diphenylsulfonebismaleimide, N,N-4,4-dicyclohexylmethanebismaleimide, N,N-α,α-4,4-dimethylenecyclohexanebismaleimide, N,N-4,4-metaxylylenebismaleimide, and N,N-4,4-diphenylcyclohexanebismaleimide. These polyimide resins may be used alone or in combination of two or more polyimide resins.

The polyphenylene oxide (PPO) resin is not particularly limited as long as the polyphenylene oxide resin is a PPO resin or a modified product of a PPO resin used as a material for various boards that can be used for production of laminates and circuit boards. Examples of the modified polyphenylene oxide include a modified polyphenylene oxide terminally modified with a substituent having a carbon-carbon unsaturated double bond, and a modified polyphenylene oxide terminally modified with a substituent having a hydroxyl group. Specific examples of the substituent having a carbon-carbon unsaturated double bond include a substituent having a vinylbenzyl group and a (meth)acrylate group. Specific examples of the substituent having a hydroxyl group include bisphenol A. These polyphenylene oxide resins may be used alone or in combination of two or more polyphenylene oxide resins.

The radically polymerizable resin is not particularly limited as long as the radically polymerizable resin is a radically polymerizable resin used as a material for various boards that can be used for production of laminates and circuit boards. Specific examples of the radically polymerizable resin include (meth)acrylic acid ester, (meth)acrylic acid diester, styrene, an epoxy (meth)acrylate resin, an unsaturated polyester resin, and a vinyl-modified PPO resin. These radically polymerizable resins may be used alone or in combination of two or more radically polymerizable resins.

It should be noted that the modified resins of the thermosetting resins described above are, for example, a phosphorus-modified epoxy resin, a phosphorus-modified phenol resin, an elastomer-modified epoxy resin, an elastomer-modified epoxy (meth)acrylate resin, a phenol-modified PPO resin, and a vinyl-modified PPO resin.

The curing agent is not particularly limited as long as the curing agent can cure the thermosetting resins described above, and examples of the curing agent include publicly known curing agents. Specific examples of the curing agent include, for a case of using an epoxy resin as the thermosetting resin, dicyandiamide, a phenolic curing agent, an acid anhydride curing agent, an aminotriazine novolac curing agent, and a cyanate resin. Particularly, in the case of using an epoxy resin as the thermosetting resin, suitably used are phenolic curing agents such as a novolac-type phenolic curing agent that is a phenolic curing agent having a novolac skeleton, and a naphthalene-type phenolic curing agent that is a phenolic curing agent having a naphthalene skeleton. In a case of using a polyimide resin as the thermosetting resin, a curing agent (cross-linker) such as polyamine is suitably used. In a case of using a PPO resin as the thermosetting resin, a cross-linker such as an epoxy resin, a radically polymerizable resin, or a monomer is suitably used, and in a case of using a radically polymerizable resin as the thermosetting resin, a radical polymerization initiator such as an organic peroxide or an azo compound is suitably used.

As another component of the resin composition, a polymer may further be added. Specific examples of the other polymer include an epoxy-modified acrylic resin, core shell rubber, polybutadiene, and a styrene-butadiene copolymer. Addition of these components gives an effect of reducing the elastic modulus of the resin composition, resulting in reduction in coefficient of linear expansion (CTE) of a cured product of the prepreg. It does not matter whether or not these components are compatible in the resin composition.

Among these components, an epoxy-modified acrylic resin and the like are preferable.

The inorganic filler that can be used in the present exemplary embodiment is not particularly limited. Examples of the inorganic filler include spherical silica, barium sulfate, silicon oxide powder, crushed silica, fired talc, barium titanate, titanium oxide, clay, alumina, mica, boehmite, zinc borate, zinc stannate, and other metal oxides and metal hydrates. Addition of such inorganic fillers to the resin composition can increase dimensional stability of a laminates. These inorganic fillers may be surface-treated with a silane coupling agent, an organic silane compound, a titanate coupling agent, or an aluminate coupling agent.

The resin composition of the present exemplary embodiment may also contain a component other than the components described above. For example, the resin composition may contain a curing accelerator. The curing accelerator is not particularly limited. There can be used, for example, imidazoles and derivatives of the imidazoles, an organophosphorus compound, metal soaps such as zinc octanoate, secondary amines, tertiary amines, and quaternary ammonium salts. The resin composition may also contain, for example, a photostabilizer, a viscosity modifier, and a flame retardant.

A ratio among the components in the resin composition is not particularly limited as long as the effects of the present disclosure can be exhibited. However, with defining a total weight of the resin components in the resin composition as 100 parts by mass, in a case of using an epoxy resin and a polyimide resin, the curing agent is preferably blended in a ratio ranging from 0.2 equivalent to 1.1 equivalent, inclusive, with respect to 1 equivalent of each of the resins. In a case of using a radically polymerizable resin, the polymerization initiator ranges from 0.5 parts by mass to 2.0 parts by mass, inclusive, with respect to 100 parts by mass of the resin. When the resin composition of the present exemplary embodiment contains an inorganic filler, a content proportion of the inorganic filler preferably ranges from about 10% by mass to about 80% by mass, inclusive, relative to a total amount of the resin composition.

Prepreg 1 according to the present exemplary embodiment includes resin layer 2 formed of a half-cured product of the resin composition described above and fibrous substrate 3 provided in resin layer 2.

Specific examples of the fibrous substrate used in the present exemplary embodiment include glass cloth, aramid cloth, polyester cloth, glass nonwoven fabric, aramid nonwoven fabric, polyester nonwoven fabric, pulp paper, and Linter paper. Use of glass cloth gives a laminate excellent in mechanical strength, and particularly, flattened glass cloth is preferable. As a material for the glass cloth, there are exemplified E-glass, S-glass, D-glass, and Q-glass that are used for electronic materials. S-glass is preferable because S-glass can reduce the difference in CTE between the board and a semiconductor chip. Flattening can specifically be performed by, for example, pressing glass cloth continuously with a pressing roll at appropriate pressure to compress yarn in a flat shape. A woven fabric substrate can be used that has a thickness ranging, for example, from 10 µm to 200 µm, inclusive.

The prepreg according to the present exemplary embodiment can be obtained as follows. The resin composition can be prepared by first blending the thermosetting resin and the curing agent that are described above, to which an additive such as a curing accelerator is added as necessary. Further, a resultant mixture can be diluted with a solvent to prepare varnish of the resin composition.

More specifically, first, components of the resin composition that can be dissolved in an organic solvent are charged into and dissolved in an organic solvent. In this procedure, heating may be performed as necessary. Then, a component that is used as necessary and is not dissolved in an organic solvent, for example, an inorganic filler is added and dispersed to a predetermined dispersion state with use of, for example, a ball mill, a bead mill, a planetary mixer, or a roll mill to prepare a varnish resin composition. The organic solvent used herein is not particularly limited. Specific examples of the organic solvent include ketone solvents such as acetone, methyl ethyl ketone, and cyclohexanone, aromatic solvents such as toluene and xylene, and nitrogen-containing solvents such as dimethylformamide.

As a method for producing a prepreg with use of the resultant resin varnish, there is exemplified a method of impregnating the fibrous substrate described above with the resultant resin varnish, followed by drying. That is, prepreg 1 according to the present exemplary embodiment is a prepreg obtained by impregnating the fibrous substrate with the resin varnish. Such prepreg 1 can produce a molded body, such as a wiring board, that sufficiently suppresses generation of the warpage.

The impregnation of the fibrous substrate described above with the resin varnish can be performed by a technique such as immersion, coating, roll coating, die coating, spraying, or bar coating. This impregnation can be repeated a plurality of times as necessary. In this procedure, it is also possible to repeat the impregnation with use of a plurality of types of resin varnish that are different in composition and concentration, for adjusting the composition and the amount of resin to finally desired composition and amount of resin.

The fibrous substrate that has been impregnated with the resin varnish is heated under desired heating conditions of, for example, a temperature ranging from 120° C. to 190° C., inclusive, and a period ranging from 3 minutes to 15 minutes, inclusive, to give a prepreg in a half-cured state (stage B).

Alternatively, as another exemplary embodiment of the prepreg, the fibrous substrate may be left as impregnated with the resin varnish, without being half-cured. In this case, the resin composition is in a state of not the stage B but a so-called stage A.

<Metal-Clad Laminate and Wiring Board>

Figure 3:
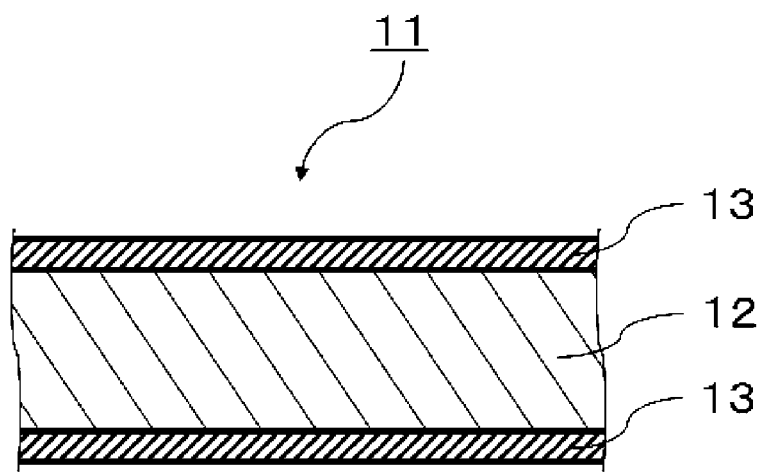
FIG. 3 is a schematic sectional view illustrating a metal-clad laminate according to an exemplary embodiment.

FIG. 3 is a schematic sectional view illustrating a metal-clad laminate according to an exemplary embodiment. Metal-clad laminate 11 includes insulating layer 12 formed of a cured product of the resin composition, and metal foil 13 disposed on one or both of upper surface of insulating layer 12 and lower surface of insulating layer 12. Such metal-clad laminate 11 can produce a wiring board that can sufficiently suppress generation of the warpage of a package.

Next, a method for manufacturing metal-clad laminate 11 with use of prepreg 1 obtained as described above is described. The method includes stacking metal foil 13, such as copper foil, on one or both of upper surface of one prepreg 1 and lower surface of one prepreg 1, or on one or both of upper surface of a stacked body of a plurality of prepregs 1 and lower surface of a stacked body of a plurality of prepregs 1. And then heat pressure molding for lamination and integration are performed to manufacture a metal-clad laminate whose one or both surfaces are clad with the metal foil. That is, metal-clad laminate 11 according to the present exemplary embodiment is a metal-clad laminate obtained by laminating metal foil 13 on prepreg 1, followed by heat pressure molding. Such metal-clad laminate 11 can produce a wiring board that sufficiently suppresses generation of the warpage.

Figure 4:
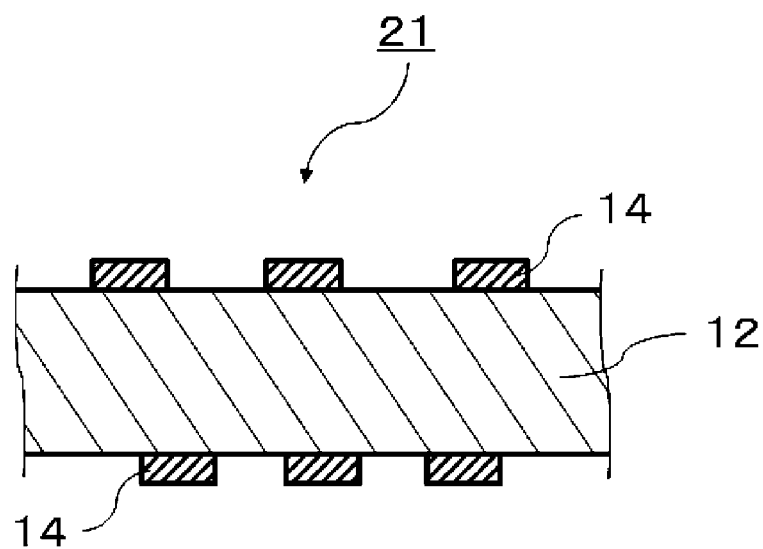
FIG. 4 is a schematic sectional view illustrating a printed wiring board according to an exemplary embodiment.

FIG. 4 is a schematic sectional view illustrating a printed wiring board according to an exemplary embodiment. Wiring board 21 is characterized by including a cured product (insulating layer 12) of prepreg 1 and conductor pattern 14 as a circuit on a surface of the cured product. A specific method for manufacturing wiring board 21 according to the present exemplary embodiment includes, for example, etching metal foil 13 on the surface of metal-clad laminate 11 described above to form a circuit and thus giving a wiring board that includes conductor pattern 14 provided as a circuit on the surface of the cured product (insulating layer 12) of prepreg 1. That is, wiring board 21 according to the present exemplary embodiment is a wiring board produced with use of prepreg 1. Such wiring board 21 can sufficiently suppress generation of the warpage even when made into a form of a package in which the wiring board is bonded to a semiconductor chip. As a technique of forming a circuit, various processes can be used, and specific examples of the technique include a subtractive process, an additive process, a semi-additive process, a chemical mechanical polishing (CMP) process, a trench process, an ink-jet process, and a method of using a conductive paste.

<Method for Measuring Thermal Stress of Wiring Board Material)

A method for measuring thermal stress of a wiring board material according to one exemplary embodiment of the present disclosure is characterized by holding a test piece of a wiring board material to be measured for thermal stress at both ends by jigs and measuring tensile stress between the jigs that is defined as thermal shrinkage stress. the tensile stress is measured during a period which a temperature of the test piece is lowered from 260° C. to normal temperature after the test piece is heated to a temperature of 260° C. while a distance between the jigs is changed in a range from 0.01 ppm/° C. to 5 ppm/° C., inclusive, by allowing the jigs to come closer to each other.

A specific process of the measurement is the same as in the tensile test performed to measure the thermal shrinkage stress of the prepreg described above.

A method for measuring thermal stress of a wiring board material according to another aspect of the present disclosure is characterized by holding a test piece of a wiring board material to be measured for thermal stress at both ends by jigs and measuring tensile stress between the jigs that is defined as thermal expansion stress. The tensile stress is measured during a period which a temperature of the test piece is raised from normal temperature to 260° C. while a distance between the jigs is changed in a range from 0.01 ppm/° C. to 5 ppm/° C., inclusive, by allowing the jigs to separate from each other.

A specific process of the measurement is the same as in the tensile test performed to measure the thermal expansion stress of the prepreg described above.

The present specification discloses various aspects of techniques as described above, from among which main techniques are summarized as follows.

A prepreg according to one aspect of the present disclosure includes a resin layer constituted by a half-cured product of a thermosetting resin composition, and a fibrous substrate provided in the resin layer. A prepreg test piece that is a cured product obtained by heat curing the thermosetting resin composition has a maximum value of 400 kPa or less for thermal shrinkage stress measured by a following thermal stress test.

[Thermal Stress Test]

A prepreg test piece having a thickness of 0.1 mm is held at both ends by jigs. And tensile stress between the jigs, which is defined as thermal shrinkage stress, is measured. The tensile stress is measured during a period which a temperature of the prepreg test piece is lowered from 260° C. to normal temperature after the prepreg test piece is heated to a temperature of 260° C. while a distance between the jigs is changed in a range from 0.01 ppm/° C. to 5 ppm/° C., inclusive, by allowing the jigs to come closer to each other.

Such a configuration can provide a prepreg capable of giving a molded body that sufficiently suppresses generation of the warpage.

Further, with regard to the prepreg, the prepreg test piece that is the cured product obtained by heat curing the thermosetting resin composition preferably has a maximum value of 100 kPa or less for thermal expansion stress measured by a following thermal stress test.

[Thermal Stress Test]

A prepreg test piece having a thickness of 0.1 mm is held at both ends by jigs. And tensile stress between the jigs, which is defined as thermal expansion stress, is measured. The tensile stress is measured during a period which a temperature of the prepreg test piece is raised from normal temperature to 260° C. while a distance between the jigs is changed in a range from 0.01 ppm/° C. to 5 ppm/° C., inclusive, by allowing the jigs to separate from each other.

Such a configuration can provide a prepreg capable of giving a molded body that more certainly suppresses generation of the warpage.

A prepreg according to another aspect of the present disclosure includes a resin layer constituted by a half-cured product of a thermosetting resin composition, and a fibrous substrate provided in the resin layer. A prepreg test piece that is a cured product obtained by heat curing the thermosetting resin composition has a maximum value of 100 kPa or less for thermal expansion stress measured by a following thermal stress test.

[Thermal Stress Test]

A prepreg test piece having a thickness of 0.1 mm is held at both ends by jigs. And tensile stress between the jigs, which is defined as thermal expansion stress, is measured. The tensile stress is measured during a period which a temperature of the prepreg test piece is raised from normal temperature to 260° C. while a distance between the jigs is changed in a range from 0.01 ppm/° C. to 5 ppm/° C., inclusive, by allowing the jigs to separate from each other.

Such a configuration can also provide a prepreg capable of giving a molded body that sufficiently suppresses generation of the warpage.

In any one of the prepregs, the thermosetting resin composition preferably contains at least one resin selected from the group consisting of an epoxy resin, a polyimide resin, polyphenylene oxide (PPO), a radically polymerizable resin, and modified resins of these resins. Further, the thermosetting resin composition preferably contains two or more resins selected from the group. This is considered to more certainly give the effects described above.

In any of the prepregs, the fibrous substrate is preferably woven fabric or nonwoven fabric. This is considered to more certainly give the effects described above. This also gives an advantage of a support having high strength.

In any one of the prepregs, the thermosetting resin composition preferably further contains an inorganic filler. This gives, in addition to the effects described above, an advantage of improving reliability due to an effect of suppressing the coefficient of linear expansion of the resin composition.

A metal-clad laminate according to an aspect of the present disclosure includes a cured product of the prepreg described above and metal foil provided on at least one of upper surface of the cured product of the prepreg and lower surface of the cured product of the prepreg. Further, the metal foil is preferably provided on both upper surface of the cured product of the prepreg and lower surface of the cured product of the prepreg. A wiring board according to an additional aspect of the present disclosure includes a cured product of the prepreg described above and a conductor pattern provided as a circuit on a surface of the cured product of the prepreg.

Such a configuration can provide a metal-clad laminate and a wiring board that can sufficiently suppress generation of the warpage even when the wiring board is made into a form of a package in which the wiring board is bonded to a semiconductor chip.

A method for measuring thermal stress of a wiring board material according to an aspect of the present disclosure is characterized by holding a test piece made of a wiring board material at both ends by jigs and measuring tensile stress between the jigs that is defined as thermal shrinkage stress. The tensile stress is measured during a period which a temperature of the test piece is lowered from 260° C. to normal temperature after the test piece is heated to a temperature of 260° C. while a distance between the jigs is changed in a range from 0.01 ppm/° C. to 5 ppm/° C., inclusive, by allowing the jigs to come closer to each other.

A method for measuring thermal stress of a wiring board material according to another aspect of the present disclosure includes holding a test piece made of a wiring board material at both ends by jigs and measuring tensile stress between the jigs that is defined as thermal expansion stress. The tensile stress is measured during a period which a temperature of the test piece is raised from normal temperature to 260° C. while a distance between the jigs is changed in a range from 0.01 ppm/° C. to 5 ppm/° C., inclusive, by allowing the jigs to separate from each other.

Such measurement methods according to the present disclosure are considered to be useful for various applications of electronic materials because the methods can easily measure the thermal stress of a wiring board.

Hereinafter, the present disclosure will be described more specifically by way of examples. A scope of the present disclosure, however, is not limited to these examples.

EXAMPLES

Example 1

A resin composition was obtained by blending 41.67 parts by mass of a naphthalene-type epoxy resin (HP9500 manufactured by DIC Corporation), 28.33 parts by mass of a naphthalene-type phenolic curing agent (HPC9500 manufactured by DIC Corporation), 30 parts by mass of an epoxy-modified acrylic resin (PMS-12-82 manufactured by Nagase ChemteX Corporation (weight molecular weight 500000)), 0.04 parts by mass of imidazole (2E4MZ: 2-ethyl-4-methylimidazole manufactured by SHIKOKU CHEMICALS CORPORATION) as a curing accelerator, and 50 parts by mass of spherical silica (SC2500GNO manufactured by Admatechs Company Limited) surface-treated with an isocyanate silane coupling agent. Subsequently, this resin composition was diluted with 151 parts by mass of methyl ethyl ketone (MEK) as a solvent to form a varnish resin composition (resin varnish).

A woven fabric substrate (glass cloth, 1078 manufactured by NITTO BOSEKI CO., LTD., thickness 43 m, unit weight 47 g/m$^2$) was impregnated with the resultant resin varnish so as to become 50 µm in thickness. And then a prepreg was produced by heating and drying the woven fabric substrate impregnated with the resin varnish at 130° C. for 6 minutes so as to be in a half-cured state.

Further, resultant two prepregs were put together. And subsequently copper foil (thickness 12 µm) as metal foil was laminated on each of both surfaces of the prepregs to form a laminated body. The laminated body was molded by pressing at 2.94 MPa (30 kgf/cm$^2$) and heating at 220° C. for 60 minutes under a vacuum condition. Thus, a 0.1-mm-thick copper-clad laminate (CCL) was produced as a metal-clad laminate.

Example 2

A prepreg was obtained in the same manner as in Example 1 except that another glass cloth, i.e., T2013 manufactured by NITTO BOSEKI CO., LTD. (thickness 71 µm, unit weight 80 g/m$^2$) was used as a woven fabric substrate and the glass cloth was impregnated with the resin varnish so as to become 0.1 mm in thickness. Further, copper foil (thickness 12 µm) as metal foil was laminated on each of both surfaces of the resultant prepreg to form a laminated body. The laminated body was molded by pressing at 2.94 MPa (30 kgf/cm$^2$) and heating at 220° C. for 60 minutes under a vacuum condition. Thus, a 0.1-mm-thick copper-clad laminate (CCL) was produced as a metal-clad laminate.

Comparative Example 1

Used as a copper-clad laminate (CCL) was commercially available MCL-E770G (manufactured by Hitachi Chemical Company, Ltd.) having a thickness of 0.1 mm.

Comparative Example 2

A resin composition was obtained by blending 41.67 parts by mass of a naphthalene-type epoxy resin (HP9500 manufactured by DIC Corporation), 28.33 parts by mass of a naphthalene-type phenolic curing agent (HPC9500 manufactured by DIC Corporation), 10 parts by mass of a core shell resin (STAPHYROID AC3355 manufactured by Aica Kogyo Co., Ltd.), 0.04 parts by mass of imidazole (2E4MZ: 2-ethyl-4-methylimidazole manufactured by SHIKOKU CHEMICALS CORPORATION) as a curing accelerator, and 120 parts by mass of spherical silica (SC2500GNO manufactured by Admatechs Company Limited) surface-treated with an isocyanate silane coupling agent. Subsequently, this resin composition was diluted with 120 parts by mass of methyl ethyl ketone (MEK) as a solvent to form a varnish resin composition (resin varnish).

A woven fabric substrate (glass cloth, 1078 manufactured by NITTO BOSEKI CO., LTD., thickness 43 µm, unit weight 47 g/m²) was impregnated with the resultant resin varnish so that thickness became 50 μm, and was heated and dried at 130° C. for 6 minutes to a half-cured state to produce a prepreg.

A 0.1-mm-thick copper-clad laminate (CCL) was produced with use of resultant prepregs in the same manner as in Example 1.

Comparative Example 3

A resin composition was obtained by blending 41.67 parts by mass of a naphthalene-type epoxy resin (HP9500 manufactured by DIC Corporation), 28.33 parts by mass of a naphthalene-type phenolic curing agent (HPC9500 manufactured by DIC Corporation), 0.04 parts by mass of imidazole (2E4MZ: 2-ethyl-4-methylimidazole manufactured by SHIKOKU CHEMICALS CORPORATION) as a curing accelerator, and 210 parts by mass of spherical silica (SC2500GNO manufactured by Admatechs Company Limited) surface-treated with an isocyanate silane coupling agent. Subsequently, this resin composition was diluted with 138 parts by mass of methyl ethyl ketone (MEK) as a solvent to form a varnish resin composition (resin varnish).

A woven fabric substrate (glass cloth, 1078 manufactured by NITTO BOSEKI CO., LTD., thickness 43 μm, unit weight 47 g/m²) was impregnated with the resultant resin varnish so as to become 50 μm in thickness. And then a prepreg was produced by heating and drying the woven fabric substrate impregnated with the resin varnish at 130° C. for 6 minutes so as to be in a half-cured state.

A 0.1-mm-thick copper-clad laminate (CCL) was produced with use of resultant prepregs in the same manner as in Example 1.

[Evaluations]

A 0.1-mm-thick prepreg test piece was obtained by removing through etching all the copper foil on the surfaces of the 0.1-mm-thick copper-clad laminate produced or arranged in the examples and comparative examples. This prepreg test piece was used for following evaluations.

(Thermal Shrinkage Stress)

The prepreg obtained in each of the examples and comparative examples was heated and dried at 220° C. for 90 minutes to form a cured product of the thermosetting resin composition in the prepreg. Subsequently, a prepreg test piece (sample) was prepared by cutting out the cured product having a thickness of 0.1 mm into 4 mm (width)×25 mm (length). The sample was held with a distance between chucks of 15 mm, by jigs for tensile measurement of a thermomechanical analysis apparatus (TMA SS6100) manufactured by Hitachi High-Technologies Corporation, and an initial load of 20 mN was applied to this sample. A tensile stress of the sample was measured during a period which a temperature of the sample is lowered from 260° C. to normal temperature at 20° C./min after the sample is heated to a temperature of 260° C. while a distance between the jigs was changed at 3 ppm/° C. in the temperature lowering time by allowing the jigs to come closer to each other.

Stress (kPa)=((Load at 30° C. (mN))−(Load at 260°
C. (mN)))/Sectional area of prepreg test piece
(mm2)

(Thermal Expansion Stress)

The prepreg obtained in each of the examples and comparative examples was heated and dried at 220° C. for 90 minutes to form a cured product of the thermosetting resin composition in the prepreg. Subsequently, a prepreg test piece (sample) was prepared by cutting out the cured product having a thickness of 0.1 mm into 4 mm (width)×25 mm (length). The sample was held with a distance between chucks of 10 mm, by jigs for tensile measurement of a thermomechanical analysis apparatus (TMA SS6100) manufactured by Hitachi High-Technologies Corporation, and an initial load of 20 mN is applied to this sample. An expansion stress of the sample was measured for expansion stress during a period which a temperature of sample is raised from room temperature to 260° C. at 20° C./min after the sample was held at room temperature for 5 minutes while a distance between the jigs is changed at 3 ppm/° C. in the temperature rising time by allowing the jigs to separate from each other.

Stress (kPa)=((Maximum load)−(Load at 30° C.
(mN)))/Sectional area of prepreg test piece
(mm²)

(Young's Modulus)

A tensile test was performed according to a method indicated in JIS K7161 and a tensile elastic modulus (Young's modulus) was derived. The measurement was performed with a prepreg test piece in a shape of type 2 described in JIS K7127.

(Tensile Elongation)

A tensile test was performed according to a method indicated in JIS K7161 and breaking elongation was measured. A cured product cut out in a width of 5 mm along a 45° direction was used as a prepreg test piece. And an initial distance between chucks was set at 60 mm.

Tensile elongation (%)=Breaking elongation/Initial
distance between chucks×100

(Coefficient of Thermal Expansion (CTE))

A prepreg test piece (sample) was prepared by cutting out the cured product having a thickness of 0.1 mm into 4 mm (width)×25 mm (length). The sample was held with a distance between chucks of 15 mm, by jigs for tensile measurement of a thermomechanical analysis apparatus (TMA SS6100) manufactured by Hitachi High-Technologies Corporation, and a load of 50 mN was applied to this sample. And a temperature of the sample was raised from room temperature to 260° C. at 10° C./min, and an amount of expansion in the temperature rising time was measured. An average coefficient of linear expansion from 50° C. to 100° C. in a resultant expansion curve was defined as a CTE.

CTE (ppm/° C.)=(ΔL/L)/(ΔT)

ΔL: amount of expansion from 50° C. to 100° C.
L: distance between chucks
ΔT: difference in temperature from 50° C. to 100° C.

(Warpage of Package)

First, a flip chip (FC) was bonded to and thus mounted on a board with a stiffener ("HCV5313HS" manufactured by Panasonic Corporation) so that a simple FC mounting package (size 16 mm×16 mm) for measuring an amount of warpage in a package was produced. Here, a Si chip in a size of 15.06 mm×15.06 mm×0.1 mm having 4356 solder balls (height 80 μm) was used as the FC. The board was prepared by removing the metal foil from the metal-clad laminate obtained in each of the examples and comparative examples. Next, the FC mounting package was measured for warpage with use of a warpage measurement system ("THERMOIRE PS200" manufactured by Akrometrix, LLC) according to a shadow moire measurement technique. The amount of warpage in the FC mounting package was evaluated for the amount of warpage measured when the package was heated from 30° C. to 260° C. and then cooled to 30° C. Evaluation criteria are as follows.

Small: warpages at 30° C. and 260° C. are 200 μm or less.
Medium: warpages at 30° C. and 260° C. are 300 μm or less.
Large: warpages at 30° C. and 260° C. are 400 μm or more.
Table 1 below shows results of the evaluations.

TABLE 1

|  |  | Example 1 | Example 2 | Comparative Example 1 | Comparative Example 2 | Comparative Example 3 |
|---|---|---|---|---|---|---|
| Shrinkage stress | kPa | 285 | 120 | 490 | 760 | 2060 |
| Expansion stress | kPa | 90 | 10 | 323 | 337 | 123 |
| Young's modulus | GPa | 7 | 7 | 25 | 11 | 23 |
| CTE | ppm/° C. | 5 | 3 | 5 | 3 | 3 |
| Tensile elongation | % | 15 | 15 | 5 | 4 | 3 |
| Warpage in PKG |  | Small | Small | Medium | Large | Large |

The results of Table 1 demonstrated that use of the prepregs according to the present disclosure sufficiently suppresses the warpage of the packages obtained by using the prepregs. Further, Example 1 showed that Example 1 is smaller in warpage of the package than Comparative Example 1 having the same CTE as the CTE of Example 1, because Example 1 is lower in Young's modulus and higher in tensile elongation than Comparative Example 1.

In contrast, the results of Comparative Examples 1 to 3 in which a conventional prepreg was used showed no sufficient suppression of the warpage.

A prepreg, a metal-clad laminate, a wiring board, and a method for measuring thermal stress of a wiring board material according to the present disclosure are useful in, for example, a wiring board used for various types of high-integrated electronic devices.

The invention claimed is:

1. A prepreg comprising
a resin layer constituted by a half-cured product of a thermosetting resin composition, and
a fibrous substrate provided in the resin layer,
wherein a maximum value of thermal shrinkage stress of 400 kPa or less is measured during a thermal shrinkage test of a test piece of the prepreg,
the test piece being a cured product obtained by heat curing the thermosetting resin composition and having a thickness of 0.1 mm,
the thermal shrinkage stress being obtained by holding the prepreg test piece at both ends by jigs and measuring, as the thermal shrinkage stress, tensile stress between the jigs, and the tensile stress being measured during a period in which a temperature of the prepreg test piece is lowered from 260° C. to normal temperature after the prepreg test piece is heated to a temperature of 260° C. while a distance between the jigs is changed in a range from 0.01 ppm/° C. to 5 ppm/° C., inclusive, by allowing the jigs to come closer to each other.

2. A prepreg comprising
a resin layer constituted by a half-cured product of a thermosetting resin composition, and
a fibrous substrate provided in the resin layer,
wherein a maximum value of thermal expansion stress of 100 kPa or less is measured during a thermal shrinkage test of a test piece of the prepreg,
the test piece being a cured product obtained by heat curing the thermosetting resin composition and having a thickness of 0.1 mm,
the thermal expansion stress being obtained by holding the prepreg test piece at both ends by jigs and measuring, as the thermal expansion stress, tensile stress between the jigs, and the tensile stress being measured during a period in which a temperature of the prepreg test piece is raised from normal temperature to 260° C. while a distance between the jigs is changed in a range from 0.01 ppm/° C. to 5 ppm/° C., inclusive, by allowing the jigs to separate from each other.

3. The prepreg according to claim 1,
wherein a maximum value of thermal expansion stress of 100 kPa or less is measured during a thermal shrinkage test of a test piece of the prepreg,
the test piece being a cured product obtained by heat curing the thermosetting resin composition and having a thickness of 0.1 mm,
the thermal expansion stress being obtained by holding the prepreg test piece at both ends by jigs and measuring, as the thermal expansion stress, tensile stress between the jigs, and the tensile stress being measured during a period in which a temperature of the prepreg test piece is raised from normal temperature to 260° C. while a distance between the jigs is changed in a range from 0.01 ppm/° C. to 5 ppm/° C., inclusive, by allowing the jigs to separate from each other.

4. The prepreg according to claim 1, wherein the thermosetting resin composition contains at least one resin selected from the group consisting of an epoxy resin, a polyimide resin, a polyphenylene oxide (PPO) resin, a radically polymerizable resin, and modified resins thereof.

5. The prepreg according to claim 1, wherein the thermosetting resin composition contains at least two resins selected from the group consisting of an epoxy resin, a polyimide resin, a polyphenylene oxide (PPO) resin, a radically polymerizable resin, and modified resins thereof.

6. The prepreg according to claim 1, wherein the fibrous substrate is woven fabric or nonwoven fabric.

7. The prepreg according to claim 1, wherein the thermosetting resin composition further contains an inorganic filler.

8. A metal-clad laminate comprising a cured product of the prepreg according to claim 1, and metal foil provided on at least one of upper surface of the cured product of the prepreg and lower surface of the cured product of the prepreg.

9. A wiring board comprising a cured product of the prepreg according to claim 1, and a conductor pattern provided as a circuit on a surface of the cured product of the prepreg.

10. A method for measuring thermal stress of a wiring board material, the method comprising:
holding both ends of a test piece constituted by the wiring board material by jigs, respectively, and
measuring tensile stress between the jigs which is defined as thermal shrinkage stress, the tensile stress being measured during a period in which a temperature of the test piece is lowered from 260° C. to normal temperature after the test piece is heated to a temperature of 260° C. while a distance between the jigs is changed in a range from 0.01 ppm/° C. to 5 ppm/° C., inclusive, by allowing the jigs to come closer to each other.

11. A method for measuring thermal stress of a wiring board material, the method comprising:
holding both ends of a test piece constituted by the wiring board material by jigs, respectively, and
measuring tensile stress between the jigs which is defined as thermal expansion stress, the tensile stress being measured during a period in which a temperature of the test piece is raised from normal temperature to 260° C. while a distance between the jigs is changed in a range from 0.01 ppm/° C. to 5 ppm/° C., inclusive, by allowing the jigs to separate from each other.

* * * * *